(12) United States Patent
Felsing et al.

(10) Patent No.: US 10,426,392 B2
(45) Date of Patent: Oct. 1, 2019

(54) SYSTEMS AND METHODS FOR DETERMINATION OF CANNABIS IMPAIRMENT USING A TRIAXIAL GYROSCOPE ASSEMBLY

(71) Applicants: Gary W. Felsing, Benicia, CA (US); Daniel K. Sunnarborg, Pleasant Hill, CA (US)

(72) Inventors: Gary W. Felsing, Benicia, CA (US); Daniel K. Sunnarborg, Pleasant Hill, CA (US)

(73) Assignee: Motus Bioengineering Inc., Benicia, CA (US)

( * ) Notice: Subject to any disclaimer, the term of this patent is extended or adjusted under 35 U.S.C. 154(b) by 0 days.

(21) Appl. No.: 15/853,459

(22) Filed: Dec. 22, 2017

(65) Prior Publication Data

US 2019/0192062 A1    Jun. 27, 2019

(51) Int. Cl.

| | |
|---|---|
| *G08B 21/00* | (2006.01) |
| *A61B 5/18* | (2006.01) |
| *A61B 5/11* | (2006.01) |
| *G01C 19/00* | (2013.01) |
| *A61B 5/00* | (2006.01) |
| *A61B 5/107* | (2006.01) |
| *G06K 9/00* | (2006.01) |

(52) U.S. Cl.
CPC .............. *A61B 5/18* (2013.01); *A61B 5/1071* (2013.01); *A61B 5/1104* (2013.01); *A61B 5/4845* (2013.01); *G01C 19/00* (2013.01); *A61B 5/1122* (2013.01); *A61B 5/1124* (2013.01); *A61B 5/74* (2013.01); *A61B 2562/0219* (2013.01); *G06K 9/00335* (2013.01)

(58) Field of Classification Search
CPC ....... A61B 5/18; A61B 5/1104; A61B 5/4845; G01C 19/00
USPC .......................................................... 340/576
See application file for complete search history.

(56) References Cited

U.S. PATENT DOCUMENTS

| | | | |
|---|---|---|---|
| 5,506,631 A * | 4/1996 | Boothe ................ | A61B 5/4863 351/200 |
| 5,573,011 A * | 11/1996 | Felsing ................ | A61B 5/1101 600/595 |
| 7,667,609 B1 | 2/2010 | Roe | |
| | | (Continued) | |

FOREIGN PATENT DOCUMENTS

WO    WO2017118980 A1    7/2017

OTHER PUBLICATIONS

Bluetooth, Wikipedia (2017).

(Continued)

*Primary Examiner* — Mark S Rushing
(74) *Attorney, Agent, or Firm* — Robert Moll (57) ABSTRACT

The invention provides systems and methods to determine cannabis impairment using gyroscopes to sense impaired movement of a suspect. The system includes a triaxial gyroscope assembly that transmits wireless signals indicative of the movement to a computing device configured to receive and store the signals and compute and display cannabis impairment of the suspect based on the signals. The method identifies cannabis impairment, including attaching a triaxial gyroscope assembly to a suspect, computing signals indicative of the movement, transmitting the signals to a computing device, and displaying an indicator of cannabis impairment on the computing device.

16 Claims, 9 Drawing Sheets

(56) References Cited

U.S. PATENT DOCUMENTS

| | | | |
|---|---|---|---|
| 9,642,317 B2 | 5/2017 | Lewis et al. | |
| 2003/0012452 A1* | 1/2003 | Trifonov | G06T 5/005 |
| | | | 382/275 |
| 2011/0270117 A1 | 11/2011 | Warwick et al. | |
| 2013/0310711 A1* | 11/2013 | Wang | A61B 5/1121 |
| | | | 600/595 |
| 2014/0052567 A1* | 2/2014 | Bhardwaj | G06Q 30/0631 |
| | | | 705/26.7 |
| 2015/0119667 A1 | 4/2015 | Reihman et al. | |
| 2016/0078708 A1 | 3/2016 | Salem | |
| 2016/0318521 A1 | 11/2016 | Nothacker et al. | |
| 2016/0327397 A1* | 11/2016 | Cordova | G06Q 40/08 |
| 2017/0055572 A1 | 3/2017 | Utley et al. | |
| 2017/0127727 A1 | 5/2017 | Davidson et al. | |
| 2017/0157343 A1 | 6/2017 | Davidson et al. | |
| 2017/0169178 A1 | 6/2017 | Beehler et al. | |
| 2017/0173262 A1* | 6/2017 | Veltz | A61M 5/1723 |
| 2017/0210289 A1 | 7/2017 | Dhawan | |
| 2018/0201131 A1* | 7/2018 | Shen | B60K 28/063 |
| 2018/0284100 A1* | 10/2018 | Agu | G01N 33/4972 |

OTHER PUBLICATIONS

Hartman, Drug Recognition Expert (DRE) examination characteristics of cannabis impairment (2016).

Blumenfeld et al., Sixty Hertz Neurostimulation Amplifies Subthalamic Neural Synchrony in Parkinson's Disease. Stanford University, Stanford, California. Published online in PLOS | One, pp. 1-12, Mar. 25, 2015.

Chen et al., Accuracy and Underlying Mechanisms of Shifting Movements in Cellists. The Department of Physiology and Neuroscience, New York University School of Medicine, New York, New York. Published online in Experimental Brain Research, DOI 10.1007/s00221-006-0483-x, Apr. 27, 2006.

Solages et al., Bilateral symmetry and coherence of subthalamic nuclei beta band activity in Parkinson's disease. Stanford University, Stanford, California. Published in Experimental Neurology 221, pp. 260-266, and available online Nov. 26, 2009.

Emborg et al., Rest Tremor in Rhesus Monkeys with MPTP-Induced Parkinsonism. Rush University, Chicago, Illinois. Published in Frontiers in Bioscience, pp. 148-154, May 1, 2003.

Koop et al., Improvement in a Quantitative Measure of Bradykinesia after Microelectrode Recording in Patients with Parkinson's Disease during Deep Brain Stimulation Surgery. Stanford University, Stanford, California. Published Movement Disorders vol. 21, No. 5, pp. 673-678, online in Wiley Interscience, DOI 10.1002/mds.20796, Jan. 26, 2006.

Koop et al., Quantitative Measures of Fine Motor, Limb, and Postural Bradykinesia in Very Early Stage, Untreated Parkinson's Disease. Stanford University, Stanford, California. Published in Movement Disorders, vol. 23, No. 9, pp. 1262-1268, 2008.

Moore et al., Concurrent Parkinson Tremors. Stanford University Medical Center, Stanford, California. Published in the Journal of Physiology 529.1, pp. 273-281, Dec. 2000.

Quinn et al., Beta Oscillations in Freely Moving Parkinson's Subjects Are Attenuated During Deep Brain Stimulation. Stanford University, Stanford, California. Published in Movement Disorders, vol. 00, No. 00, 2015.

Romanelli et al., Microelectrode recording revealing a somatotopic body map in the subthalmic nucleus in humans with Parkinson disease. Stanford University, Stanford, California. Published in Journal of Neurosurgery 100, pp. 611-618, 2004.

Wingeier et al., Intra-operative STN DBS Attenuates the Prominent Beta Rhythm in the STN in Parkinson's Disease. Department of Neurology and Neurosciences Institute, Stanford University, Stanford, California. Published in Experimental Neurology 197, pp. 244-251, Jan. 1, 2006.

\* cited by examiner

SYSTEMS AND METHODS FOR DETERMINATION OF CANNABIS IMPAIRMENT USING A TRIAXIAL GYROSCOPE ASSEMBLY

BACKGROUND

The invention relates to systems and methods for determination of *cannabis* impairment. In particular, the invention determines *cannabis* impairment by using a gyroscope assembly to sense the movement of a suspect and a computing device to analyze the movement during the performance of tests.

Driving under the influence of drugs has increased, while driving under the influence (DUI) of alcohol has decreased in recent decades according to Hartman et al., *Drug Recognition Expert (DRE) Examination Characteristics of Cannabis Impairment* (2016)("Hartman"), which is hereby incorporated by reference herein.

With the legalization of marijuana in various states, *cannabis* has become a more common drug detected in drivers. Although *cannabis* use may be legal in certain states, it still can impair driving ability. Driving while *cannabis* impaired has been associated with approximately double the crash risk. See Hartman at page 220.

If an officer observes a person that may be impaired and who smells of marijuana, it is difficult to determine if that person is *cannabis* impaired to an extent that the law considers unsafe for certain activities such as driving a car.

Unlike blood alcohol content, THC content in blood is not a reliable measure of *cannabis* impairment. There is no detectable difference in *cannabis* impairment between a suspect with <5 µg/L and ≥5 µg/L blood THC. Hartman, at page 227.

Thus, determining if a person is *cannabis* impaired may involve several steps. First, an officer may observe signs (e.g., weaving or driving too slowly) and the driver has other symptoms (e.g., bloodshot eyes and smells of marijuana) that indicate a person is a suspect who should be checked for *cannabis* impairment. To establish if it is *cannabis* impairment, the officer may perform an evaluation that includes certain psychophysical tests (e.g., the modified Romberg balance test, the walk and turn, the one leg stand, and finger to nose).

In each psychophysical test, the officer states the instructions to the suspect and then asks the suspect to perform the test. Each test seeks to challenge the suspect's coordination, ability to divide attention and to follow directions. Many impairment clues depend on the officer's subjective evaluation and strict attention. The officer may be distracted by cars speeding nearby and suspect's behavior. Further, observations at night in poor lighting may hinder accurate observations of test performance. Further, the officer must accurately recall what he observed sometimes months later in court. To the inventors' understanding no one has used gyroscopes to quantify the movement while conducting psychophysical tests of a suspect for *cannabis* impairment.

SUMMARY OF THE INVENTION

The present invention provides systems and methods of determination of *cannabis* impairment using a computing device communicating with gyroscopes to sense movement of a suspect being tested for *cannabis* impairment.

In a feature of the invention, the system for determination of *cannabis* impairment includes a gyroscope assembly configured to attach to the suspect to sense the suspect's movement and transmit signals indicative of the suspect movement in accordance with a communication protocol; and a computing device, spaced apart from the gyroscope assembly, configured to receive and store the signals and indicate *cannabis* impairment based on the signals.

In a feature of the invention, the method for identifying a suspect with *cannabis* impairment, comprises attaching a gyroscope assembly to a suspect to sense the angular rate of the suspect's movement, computing signals indicative of the suspect's movement in the gyroscope assembly, transmitting the signals in accordance with a communication protocol, receiving the signal in a computing device spaced apart from the gyroscope assembly, storing in the computing device an indicator of *cannabis* impairment of the suspect based on the signals, and displaying the indicator of *cannabis* impairment on the computing device.

In another feature of the invention, the systems and methods use a triaxial gyroscope insensitive to earth's gravitational field which measures movement of a body part without regard to orientation during psychophysical tests.

In still another feature of the invention, the triaxial gyroscope assembly and/or computing device is configured to use the Root Sum Squared (RSS) equation on the signals of the gyroscopes to indicate the magnitude of the human movement indicative of the *cannabis* impairment.

In another feature, the method quantifies the suspect's movement such as sway as defined in the one leg stand test, sway and balance as defined in the modified Romberg balance test, gait as defined in the walk and turn test, and hand movement as defined in the finger to nose test as indicators of *cannabis* impairment.

DETAILED DESCRIPTION OF THE PREFERRED EMBODIMENTS

The following description includes the best mode of carrying out the invention. The detailed description illustrates the principles of the invention and should not be taken in a limiting sense. The scope of the invention is determined by reference to the claims. Each part (or step) is assigned its own part (or step) number throughout the specification and drawings. The method drawings illustrate a specific sequence of steps, but the steps can be performed in parallel and/or in different sequence to achieve the same result.

The user of the system will often be a law enforcement officer (i.e., an officer) who seeks to confirm observations (e.g., visual, auditory, smell) out in the field on whether a suspect is *cannabis* impaired. For brevity, we refer to the user as an officer.

Figure 1:
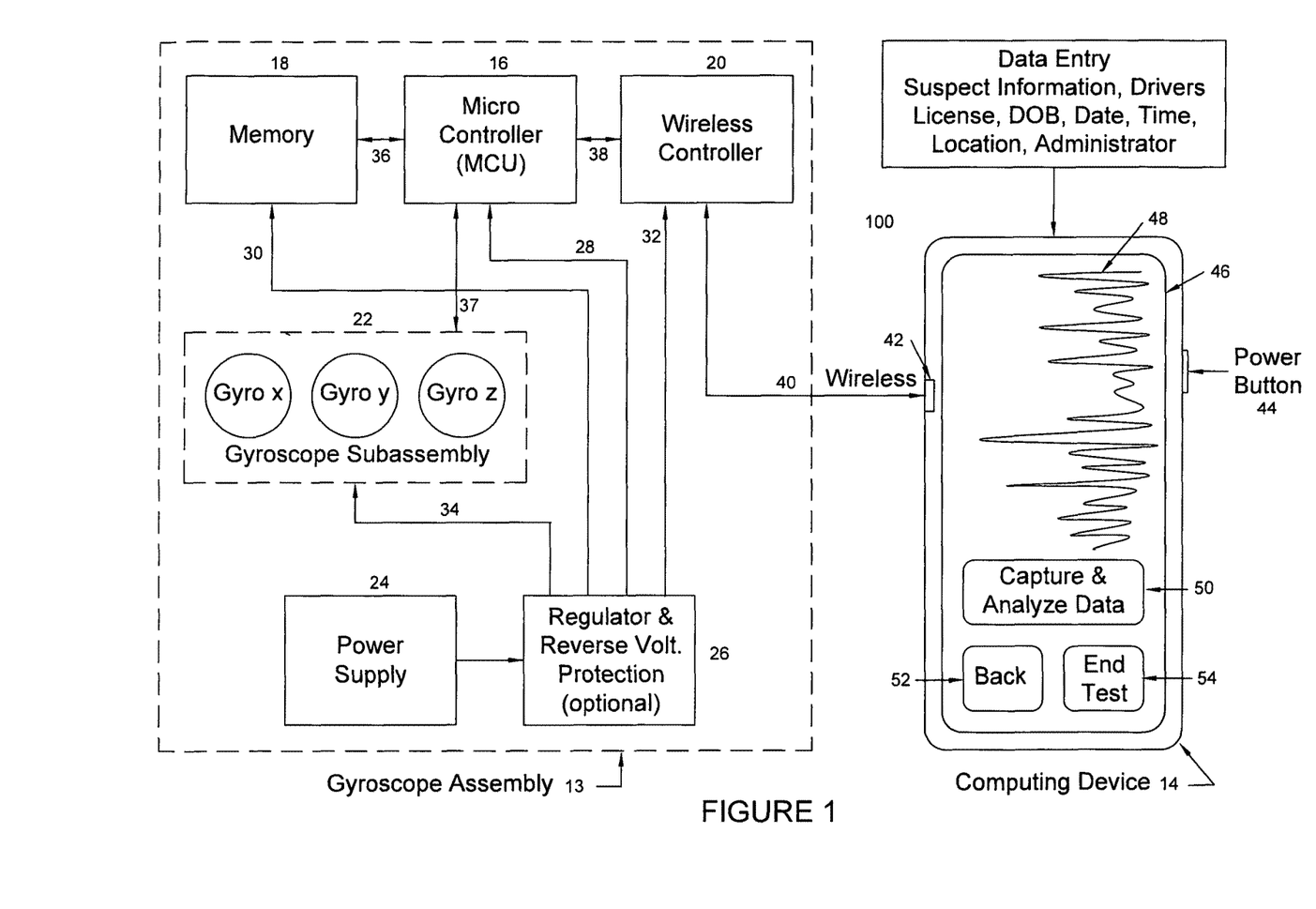
FIG. 1 is a hardware architecture for the system of determination of *cannabis* impairment.

FIG. 1 illustrates a hardware architecture for the system. As shown, the system 100 includes a gyroscope assembly 13 and a computing device 14. A gyroscope assembly 13 is secured to the suspect and communicates signals indicating movement of the suspect to a computing device 14. The computing device analyzes and displays results during tests to determine if the suspect is *cannabis* impaired. In an embodiment, the gyroscope assembly 13 includes a microcontroller 16, a memory 18, a wireless controller 20, a gyroscope subassembly 22, and a source of regulated DC power 24, 26. As shown, the gyroscope subassembly 22 is preferably a triaxial gyroscope. A suitable microcontroller is Microchip Technology part no. PIC24F32KA302, a suitable memory is Microchip Part No. SST26VF064B, and a suitable wireless controller is Microchip Technology Part No. RN4871, all available from Microchip Technology, Inc. Chandler, Ariz. A suitable power source is the CR2032 battery made by Duracell, Energizer, and other manufacturers. Favorable results can be achieved using a small solid state triaxial orthogonal micro-gyroscope of silicon manufactured by TDK InvenSense Inc., San Jose, Calif., such as the Model No. MPU-9250.

The triaxial gyroscope assembly is programmed using C and assembly language in the Integrated Development Environment (IDE) from Microchip Technology, Inc. Chandler, Ariz. Code examples, webinars, and training for programming the MCU peripherals are provided by Microchip Technology, Inc. Third party books and IDE add-ons are also available and used as reference for coding. The tools in the IDE convert the programming language to machine language providing instructions that the microprocessor can execute. Reese et al, *Microcontrollers: From Assembly Language to C Using the PIC24 Family* describes PIC24 programming in detail, which is hereby incorporated referenced by reference herein.

Hennessy and Patterson, *Computer Architecture: A Quantitative Approach* (2012), and Patterson and Hennessy, *Computer Organization and Design: The Hardware/Software Interface* (2013) describe known hardware and software, storage systems, caching, and networks and are hereby incorporated by reference herein. Data is defined as including user data, instructions, and metadata. We define non-transitory computer-readable medium as any suitable storage device such as a USB flash drive.

In the illustrated embodiment, a power supply 24 and a regulator and reverse voltage protection circuit 26 is the source of regulated DC power. In an alternative embodiment, the power supply 24 includes a built-in voltage regulator and reverse voltage protection circuit. In another, the power supply 24 is provided by AC power then converted to DC. In all embodiments, the power supply 24 is the source of the DC power delivered on lines 28, 30, 32, and 34, to respectively the microcontroller 16, the memory 18, the wireless controller 20, and the gyroscope subassembly 22.

Once power is supplied, the microcontroller 16 communicates on a bus 36 with the memory 18, on a bus 37 with the gyroscope subassembly 22, and on a bus 38 with the wireless controller 20. The digital output of the gyroscope subassembly 22 is read by the microcontroller 16, formatted, and sent to the wireless controller 20. The wireless controller communicates wirelessly through a communication interface 42, along wireless path 40 to the computing device 14. The digital output from the gyroscope assembly 13 indicates the physical movement of the suspect. For example, if the gyroscope assembly 13 is attached to the suspect's hand, the data will indicate the magnitude and frequency of hand movement during the test.

In an embodiment, the Bluetooth technology is suitable for implementing the wireless communication, and described in detail in the Bluetooth article in Wikipedia (2017), which is hereby incorporated by reference herein. A wireless controller 20 of the gyroscope assembly 13 will sense the computing device 14 is nearby and set up a network connection between the devices. Once the connection is made, synchronization between the devices occurs.

Although using a triaxial gyroscope for the gyroscope subassembly 22 is a preferred choice for the system, any gyroscope subassembly can be used if it: (1) senses motion accurately over a range of frequencies, temperatures and time period equal or greater than the time of the tests, (2) is sufficiently small and light to allow the hand or other body part to move naturally and unrestricted, and (3) is inherently insensitive to its orientation in earth's gravitational field and can sense the inertial angular rate of motion without being tied to a fixed reference.

FIG. 1 illustrates a computing device 14 that is a conventional cell phone (e.g., Android based phone) having adequate computational power and data storage. In other embodiments, the computing device 14 is a tablet (e.g., iPad®), a laptop, or a smart watch. In others, the computing device 14 may be a low costsingle board computer mounted in a vehicle (e.g., police car).

The computing device 14 includes a user interface 46 displaying a plot of suspect movement 48, a capture & analyze data button 50, a back button 52, an end test 54, and a power button 44. When the computing device 14 is turned on and the application launched, a software application defines the state of the application, the screen displayed, data entry of suspect information, the test selected, processing and analysis of gyroscope subassembly output received, and display of that suspect's movement.

The software application of the computing device 14 can be written in a variety of languages. If an Android device, *Medinieks, Programming Android: Java Programming for the New Generation of Mobil Devices* (2012) is a useful reference that describes Android programming and is hereby incorporated by reference herein. If an Apple device, Mathias, *Swift Programming: The Big Nerd Ranch Guide* (2nd Edition) describes Android programming in detail and is hereby incorporated by reference herein.

The computing device 14 has a processor for executing the software application. The computing device 14 includes a processor (e.g., multicore processors designed and/or made by Intel, ARM or AMD). The type of processor is not essential to the invention. The computing device 14 includes a communication interface 42, an operating system to manage operation of the processor(s), the application, the user interface of the application, and communications between the computing device 14 and the triaxial gyroscope assembly 13.

Google Android, Apple iOS, or Windows Phone are each suitable for use as an operating system running on the computing device 14 and are not essential to the invention.

Tanenbaum, *Modern Operating Systems* (2016) describes the details of operating systems and is hereby incorporated by reference herein.

Figure 2A:
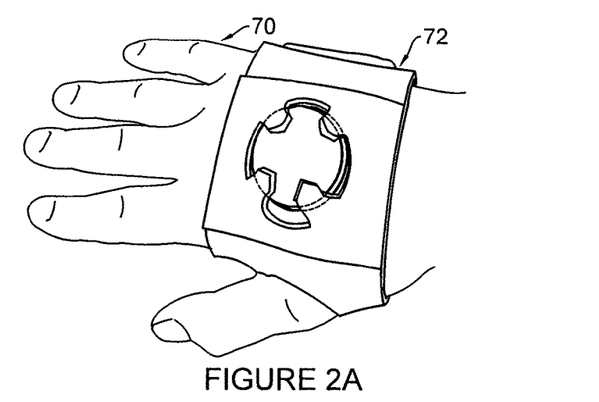
FIG. 2A illustrates a glove with a gyroscope assembly on a hand.
Figure 2B:
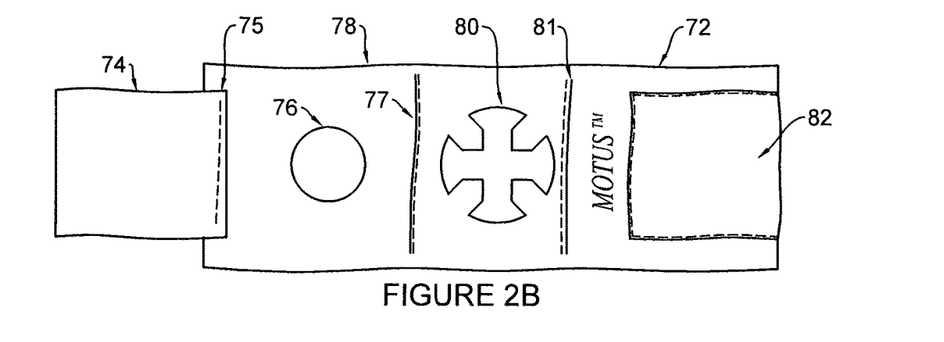
FIG. 2B illustrates a strap to secure the gyroscope assembly to the hand or ankle of a suspect.
Figure 2C:
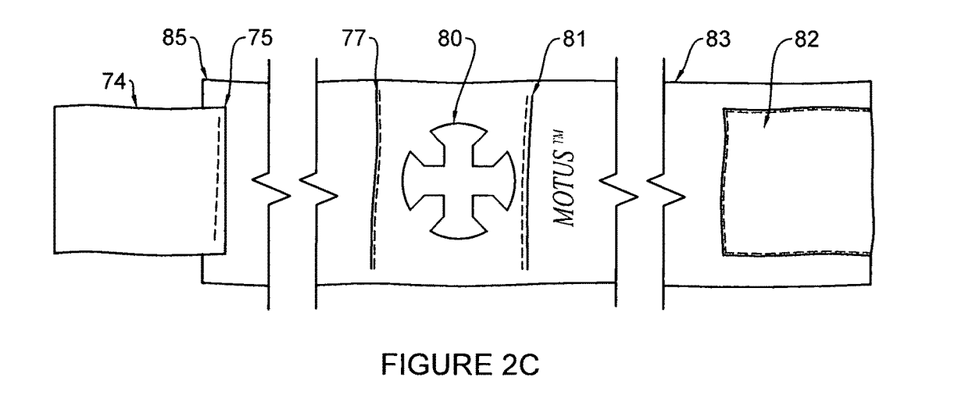
FIG. 2C illustrates a strap to secure the gyroscope assembly to the head, leg, chest, or trunk of a suspect.

Various attachments can secure the gyroscope assembly to the body of the suspect. FIG. 2A illustrates a strap 72 securing the gyroscope assembly on a hand 70. The strap 72 is ambidextrous, fingerless, has a thumb hole 76 in section 78, and a pocket 80 for the gyroscope assembly. FIG. 2B illustrates the strap of FIG. 2A apart from the hand with the gyroscope assembly pocket 80. The strap includes stitching 75, 77, and 81. The strap also includes Velcro® ends 74 and 82, a thumb hole 76, and a pocket 80 surrounding by foam to protect the gyroscope assembly. The strap can be secured to the ankle or hand. FIG. 2C illustrates a strap 83 and 85 identical to the strap of FIG. 2B (including parts 74, 75, 77, 80, 81, and 82), but longer (e.g., three feet) to secure the gyroscope assembly to the head or chest. The broken lines of the strap indicate it's not drawn to scale.

An officer may employ the system during psychophysical tests to quantify a suspect's movement to confirm *cannabis* impairment. Hartman et al., *Drug Recognition Expert (DRE) Examination Characteristics of Cannabis Impairment* (2016), which is hereby incorporated by reference herein, state that if an officer observes ≥2 failures in performing the following psychophysical tests that may indicate *cannabis* impairment. The system will confirm whether the officer's observations are in fact the case.

The finger to nose test can be used to detect *cannabis* impairment in the following manner. After a gyroscope assembly 13 is secured to the suspect's hand by the strap of FIG. 2B, the officer will instruct the suspect to touch the tip of his or her nose with the tip of the index finger six times (three times per hand). The system quantifies how many times the suspect fails to touch the nose.

The one leg stand test can be used to detect *cannabis* impairment in the following manner. After a gyroscope assembly 13 is secured by the strap of FIG. 2C to the suspect's chest or head, the officer will instruct the suspect to stand on one foot with the other foot about 6-inches off the floor and count aloud, e.g., 30 seconds or until told to put the foot down while being timed. The system quantifies the motion of suspect swaying, hopping, or putting the foot down during the test, body tremors, and inaccurate estimates of the time.

The walk and turn test can be used to detect *cannabis* impairment in the following manner. After a gyroscope assembly 13 is secured by the strap of FIG. 2B or FIG. 2C, respectively, to the suspect's ankle or chest, the officer will instruct the suspect to take nine heel-to-toe steps along a straight line, count the steps aloud, then turn 180-degree and walk back along the same line. The system quantifies when the suspect loses balance, stops while walking, does not walk heel-to-toe, strays off the line, takes a wrong number of steps, does an incorrect 180-degree turn, and has body tremors.

The modified Romberg balance test can be used to detect *cannabis* impairment in the following manner. After the gyroscope assembly 13 is secured to the suspect's chest or head, the officer will instruct the suspect to stand with feet together, then tilt the head backward with eyes closed, and estimate the passage of 30 seconds. This detects an inability to maintain a steady standing posture with eyes closed, as well as divide attention to estimate the time. The system quantifies sway, inaccurate time estimates, and body tremors during the test.

FIGS. 3A-3D illustrates the display screens of a user interface on a computing device seen by an officer conducting *cannabis* impairment tests.

Figures 3A, 3B:
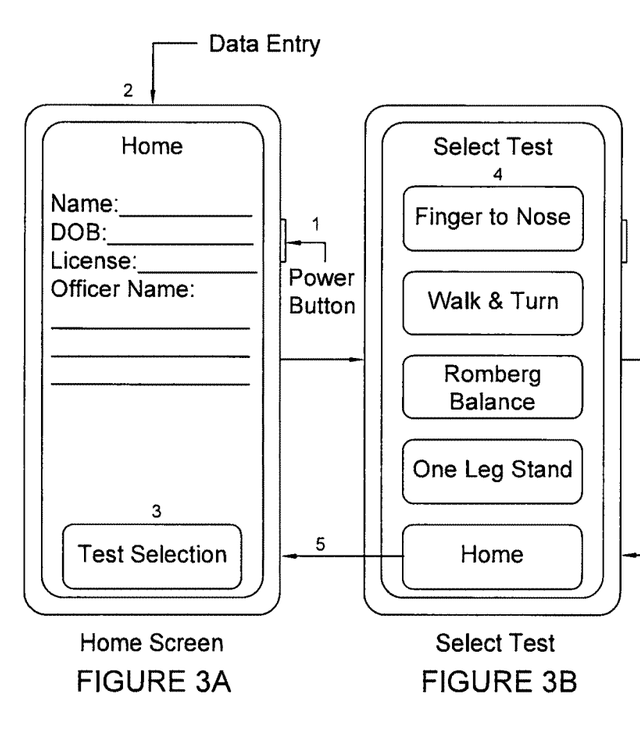
FIGS. 3A-3D illustrates a user interface on a computing device used by an officer conducting *cannabis* impairment tests.

FIG. 3A illustrates a home screen that displays a data entry section and a test selection button. The officer turns on the computing device 14 (FIG. 1) by pushing the power button at step 1. At step 2, the officer manually enters or scans data identifying the suspect (e.g., name, date of birth (DOB), and license, e.g., driver license or ID card) and the officer name. In an embodiment, the computing device 14 uses GPS to identify the location. When the officer selects the test selection button at step 3, the application displays the screen shown in FIG. 3B.

FIG. 3B illustrates a screen that displays a set of user selectable buttons to select a psychophysical test (e.g., finger to nose, walk and turn, modified Romberg balances, one leg stand) and a user selectable button to return to the home screen. If the officer selects a test button at step 4, the application displays the screen shown in FIG. 3C. If the officer selects the home button, the application returns along path 5 and displays the screen shown in FIG. 3A.

Figure 3C:
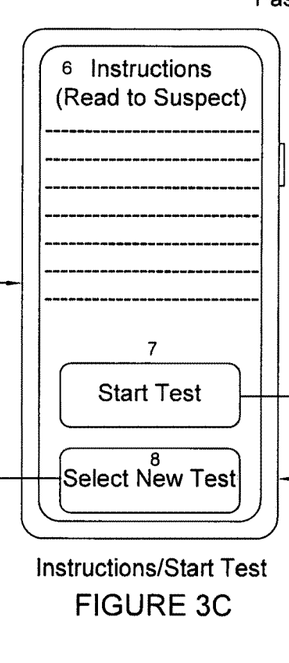

FIG. 3C illustrates a screen displaying instructions the officer reads to the suspect specific to the test selected in FIG. 3B, a start test button, and a select new test button. At step 6, the officer reads the instructions so the suspect understands what the test requires and explains why the officer is securing the gyroscope assembly to the suspect. If the officer selects the start test button at step 7, the application starts a network process to transmit the digital data output from the gyroscope assembly 13 to the computing device 14, performs a RSS computation of the digital data output and displays a RSS plot of the data (FIG. 1). If the officer selects the start new test button at step 8, the application displays the screen of FIG. 3B.

Figure 3D:
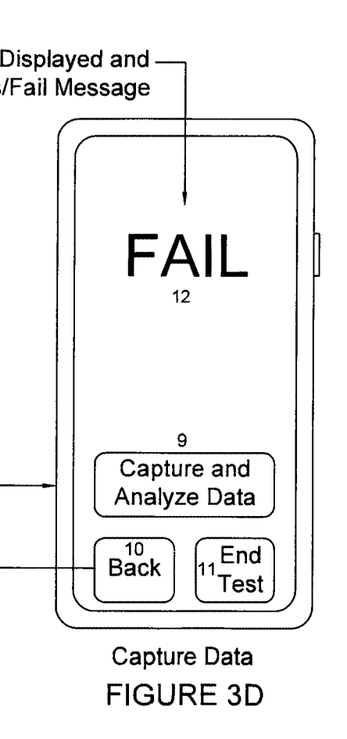

FIG. 3D illustrates a screen that displays the results of the test (e.g., pass or fail), a capture and analyze data button, a back button, and an end test button. If the officer selects the capture and analyze button at step 9, the application saves the digital data output of gyroscope assembly 13 required for the test. If the officer selects the back button at step 10, the application will display the screen shown in FIG. 3C. If the officer selects the end test button at step 11, the application will display the results of all the tests 12. In an embodiment, if the suspect's body movement in two or more of the four psychophysical tests fails as defined in the Hartman article, the computing device 14 will display and/or sound the test results that the suspect is *cannabis* impaired. In an embodiment, the test results are conveyed as an auditory message through the speaker of the computing device, or displayed as a text message (e.g., PASS or FAIL), and/or a color (e.g., Pass=green and Fail=red).

Figure 4:
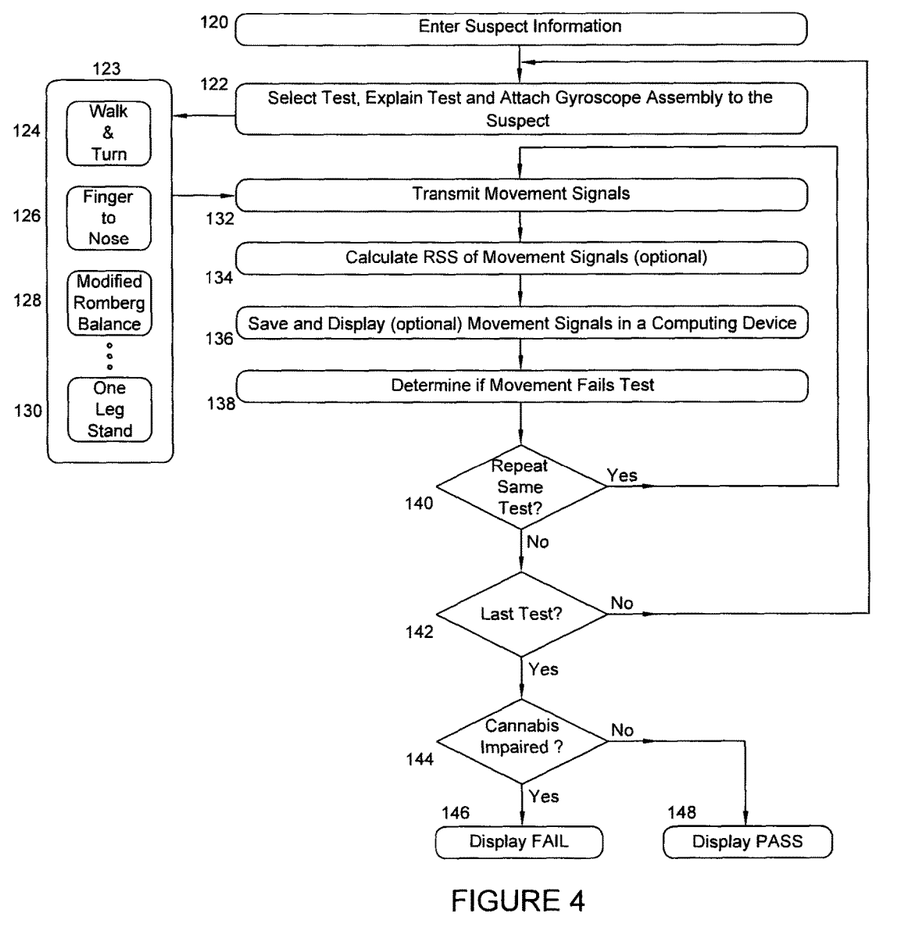
FIG. 4 is a flowchart of a method of determination of *cannabis* impairment.

FIG. 4 is a flowchart of the overall method of determination of *cannabis* impairment. At step 120, an officer enters suspect information in the screen of FIG. 3A. At step 122, the officer selects a test from a list of tests 123 using the buttons on the screen of FIG. 3B. For example, the officer can select the walk and turn test 124, finger to nose test 126, modified Romberg balance test 128, or the one leg stand test 130, then explain the test and attach the gyroscope assembly to the suspect. At step 132, the gyroscope assembly 13 transmits the signals indicative of the suspect's movement during the test. At step 134, the computing device 14 calculates the RSS of the digital data signals of gyro x, gyro y, and gyro z of the gyroscope subassembly. At step 136, the computing device 14 saves and displays (optional) the movement signals in the computing device 14. At step 138, the computing device 14 determines if the movement fails the test. At step 140, the officer decides whether to repeat the test. If yes, the method repeats steps 132, 134, 136, and 138. If the officer decides to not repeat the test, the method proceeds to step 142 where the officer decides if testing is complete. If not, the method returns to step 122, the officer selects a test, and steps 132, 134, 136, 138, and 140 are repeated. If yes, testing is complete and the test result computed at step 144 and displays FAIL (i.e., impaired) at step 146 or PASS (i.e., not impaired) at step 148.

Figure 5:
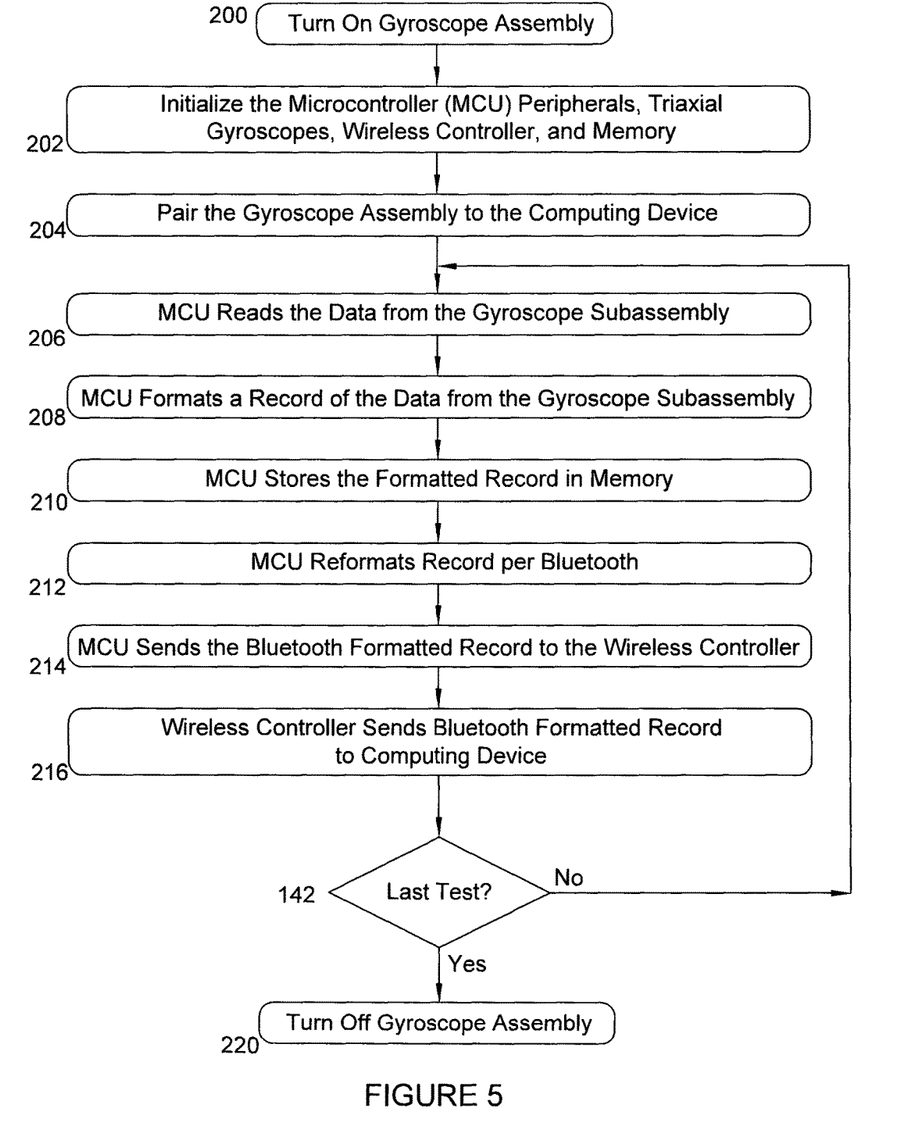
FIG. 5 illustrates a method of operation for the gyroscope assembly and the computing device shown in FIG. 1.

FIG. 5 illustrates a method of operation for the gyroscope assembly and the computing device shown in FIG. 1. After turning on the system at step 200, the microcontroller (MCU) 16 initializes a gyroscope subassembly (e.g., triaxial gyroscope) 22, a wireless controller 20, and a memory 18 at step 202. At step 204, the wireless controller 20 of the gyroscope assembly 13 is paired to communicate with the computing device 14 according to the Bluetooth protocol. See the details in Bluetooth Wikipedia (2017) article, which is hereby incorporated by reference herein. At step 206, the MCU 16 reads the output data of the gyroscope subassembly 22. At step 208, the MCU 16 formats a record of the output data from the gyroscope subassembly 22. At step 210, the MCU 16 stores the formatted record in the memory 18. At step 212, the MCU 16 reformats the record for transmission according to the Bluetooth transmission. At step 214, the MCU 16 sends the Bluetooth formatted record to the wireless controller 20. At step 216, the wireless controller 20 sends the Bluetooth formatted record on the wireless path 40 to the computing device 14.

At step 142, the method checks if the officer has completed the last test to determine *cannabis* impairment. If so, the method turns off the gyroscope assembly 13 at step 220. If not, the method returns to read the gyroscope output data at step 206, format the record of the data at step 208, store the formatted record in the memory at step 210, reformat the record per Bluetooth at step 212, send the Bluetooth formatted record to the wireless controller at step 214, and the wireless controller sends the Bluetooth formatted record to the computing device at step 216.

Figure 6:
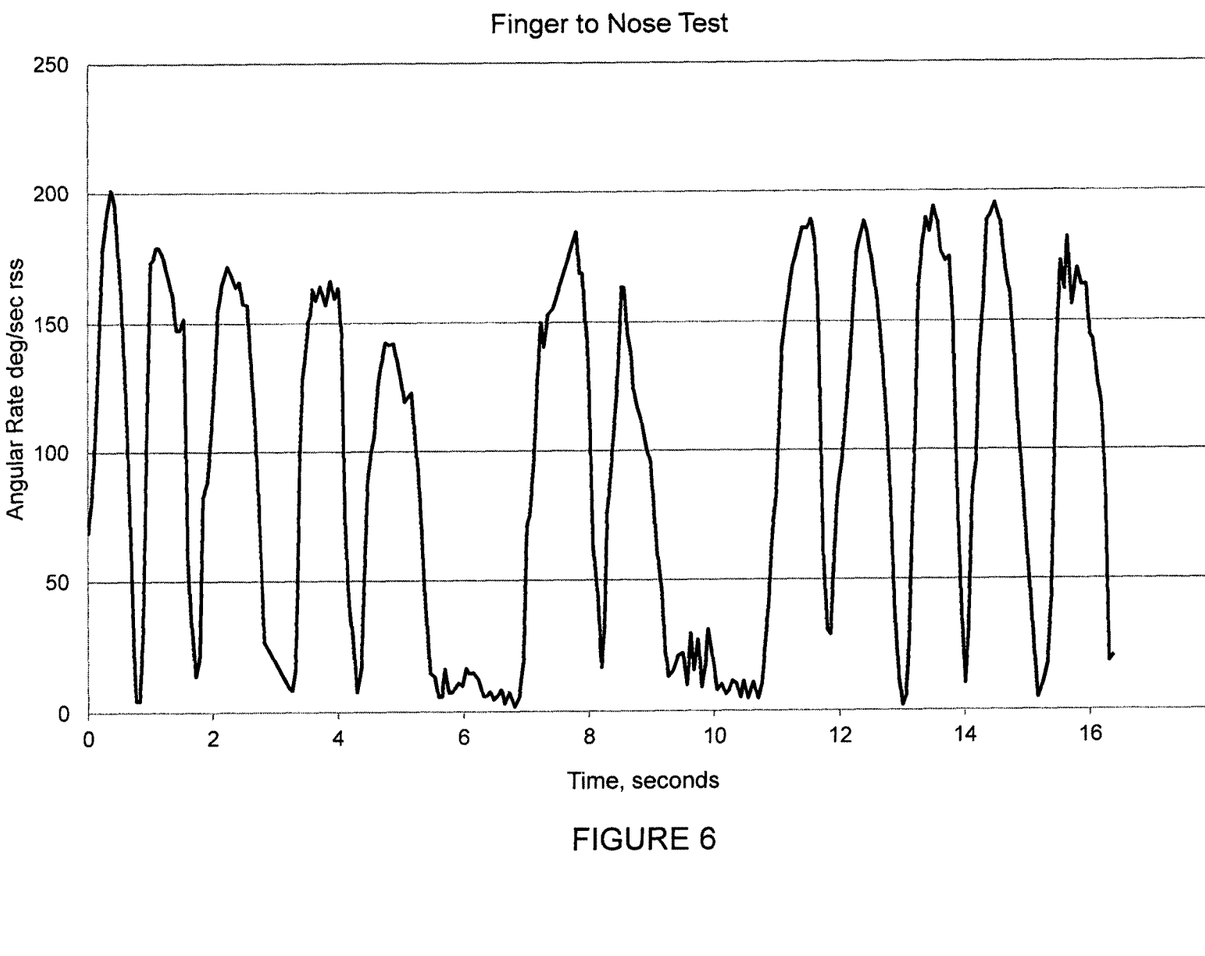
FIG. 6 illustrates a plot of RSS angular rate versus time for the finger to nose test.

FIG. 6 illustrates a plot of RSS angular rate versus time for the finger to nose test. The plot illustrates normal and abnormal finger to nose test data with the gyroscope assembly mounted on the hand. There are minimums when the arm is extended (essentially zero angular velocity) and when the finger touches the nose (also essentially zero angular velocity). When the subject is impaired, we would expect that the nose is initially missed as shown, and the trace erratic, horizontal and near zero. Thus, FIG. 6 shows successful nose touches followed by two misses near six and ten seconds. This is followed by additional successful nose touches.

Figure 7:
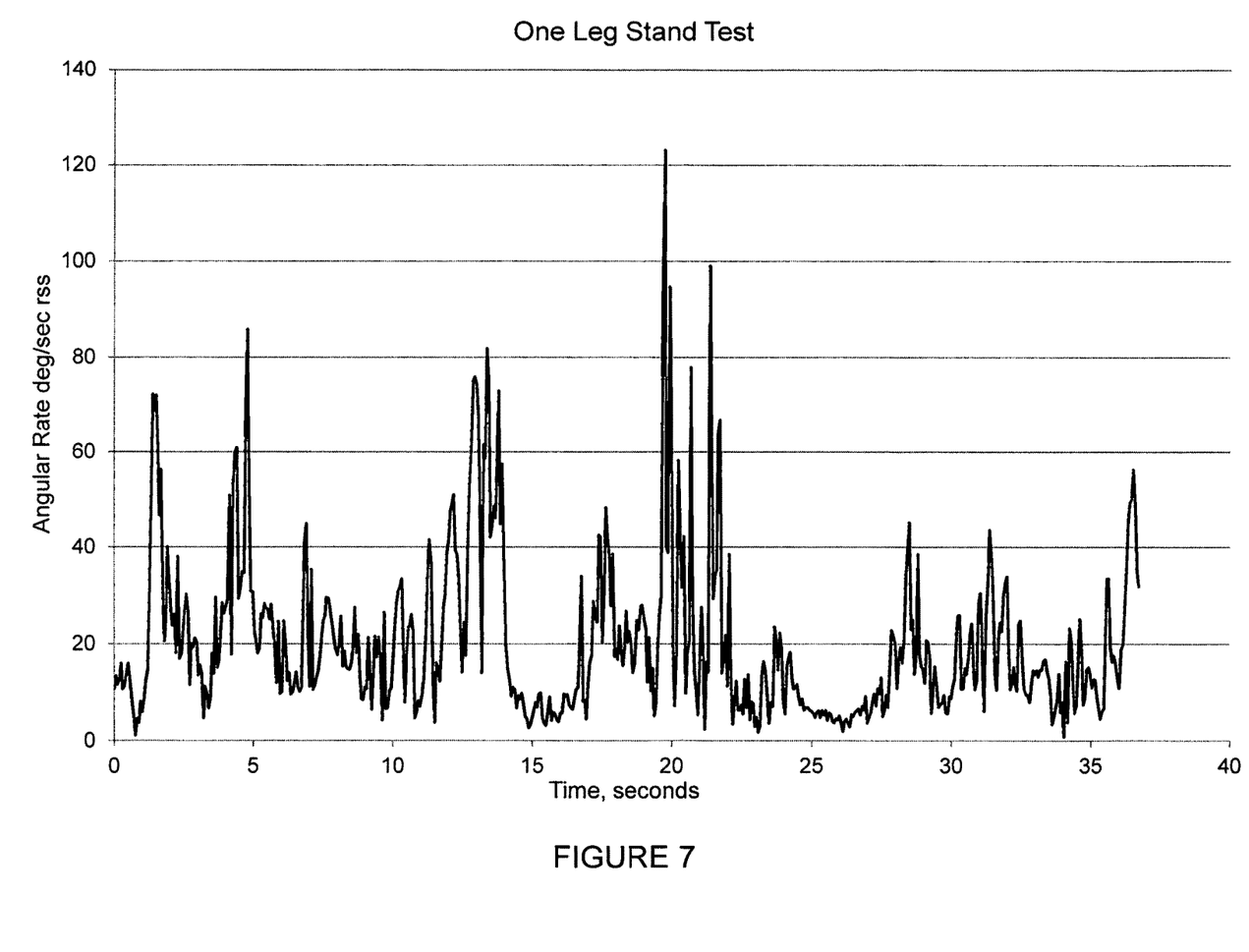
FIG. 7 is a plot of RSS angular rate versus time for the one leg stand.

FIG. 7 is a plot of RSS angular rate versus time for the one leg stand. As shown, the one leg stand data with the gyroscopes mounted on the chest or head displays excessive movement that we would expect in testing a suspect that is impaired. With perfect balance the trace would be flat and near zero over the course of the test. Normally there will be some sway, but with impairment the values of angular rate will become higher. In the example shown, there would be a value (e.g., 40 or 60 degrees/seconds), set by the authorities, above which would constitute impairment.

Figure 8:
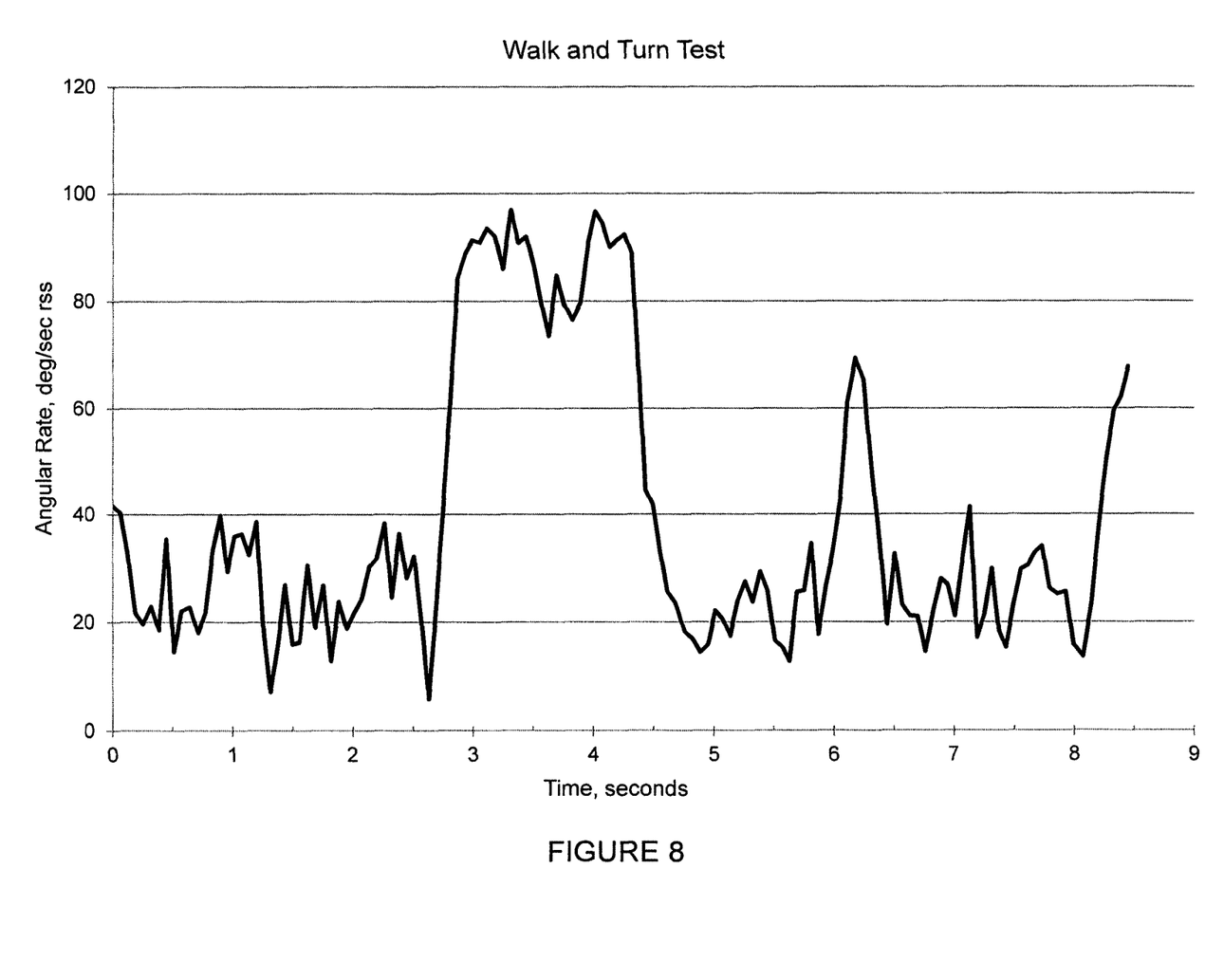
FIG. 8 is a plot of RSS angular rate versus time for the walk and turn test.

FIG. 8 is a plot of RSS angular rate versus time for the walk and turn test. As shown, the walk and turn data with the gyroscopes mounted on the chest or head displays relatively low levels of movement associated with each step followed by the 180-degree turn which is much higher between 2.5 and 4.5 seconds. This is then followed by a local peak around 6 seconds which indicates loss of balance. The number and value of these peaks can be used as an indication of impairment. In the example shown, there would be a value (e.g., 40 or 60 degrees/seconds) set by the authorities, above which would constitute impairment.

Figure 9:
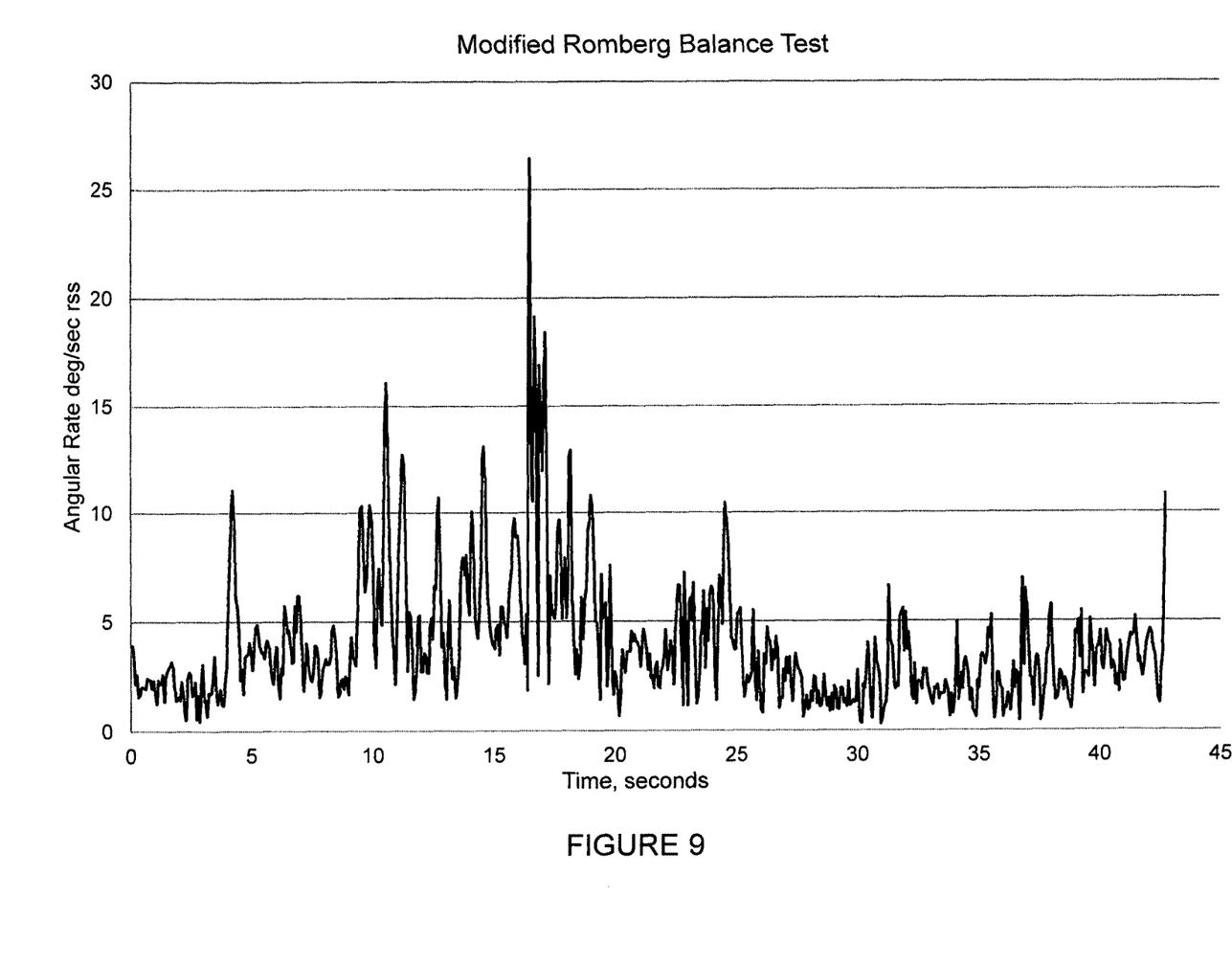
FIG. 9 is a plot of RSS angular rate versus time for the modified Romberg balance test.

FIG. 9 is a plot of RSS angular rate vs. time for the modified Romberg balance test. As shown, the modified Romberg balance data with the gyroscopes mounted on the chest or head displays excessive movement that we would expect in testing a suspect that is impaired. With perfect balance the trace would be flat and near zero over the course of the test. Normally there will be some sway, but with impairment the values of angular rate will become higher. In the example shown, there would be a value (e.g., 15 or 20 degrees/seconds), set by the authorities, above which would constitute impairment.

What is claimed is:

1. A system for a law enforcement officer's determination of *cannabis* impairment of a suspect having THC content, comprising:
    a triaxial gyroscope assembly configured to attach to a suspect to sense the angular rate of the suspect's movement and transmit signals indicative of the suspect's movement in accordance with a wireless communication protocol; and
    a computing device, spaced apart from the triaxial gyroscope assembly, configured to receive and store the signals indicative of the suspect's movement during the law enforcement officer's application of predetermined psychophysical tests, wherein the tests include a finger to nose test, a walk and turn test, a modified Romberg balance test, and a one leg stand test on the suspect, and to use the root sum squared (RSS) equation on the signals indicative of the suspect's movement to display RSS signals of the angular rate of movement versus time and to quantify the number of failures on each test demonstrated by abnormal and excessive suspect movement test data obtained during performance of the tests that indicate *cannabis* impairment rather than THC content of the suspect.

2. The system of claim 1, wherein the computing device is configured to quantify the motion of the suspect by taking a weighted average of the signals of the RSS equation over the duration of a test to indicate the *cannabis* impairment.

3. The system of claim 1, wherein the computing device is configured to use the Root Sum Squared (RSS) equation on the signals of the triaxial gyroscope assembly to indicate the *cannabis* impairment.

4. The system of claim 3, wherein the computing device is configured to quantify the motion of the suspect by taking a weighted average of the signals of the RSS equation over the duration of a test to indicate the *cannabis* impairment.

5. The system of claim 1, wherein the triaxial gyroscope assembly includes a low pass filter configured with a frequency response from DC up to 50 Hertz.

6. The system of claim 1, wherein the computing device is configured to receive identifying information of the suspect and a test administrator.

7. The system of claim 1, wherein the computing device is configured to display a real-time strip chart of the suspect's movement with adjustable limits displayed that are associated with the *cannabis* impairment.

8. The system of claim 1, wherein the indicator of the *cannabis* impairment is displayed and/or sounded on the computing device.

9. A method for testing a suspect for *cannabis* impairment using a triaxial gyroscope assembly that communicates with a computing device, comprising:
- attaching a triaxial gyroscope assembly that outputs data indicative of the angular rate of the suspect's movement during a set of psychophysical tests, wherein the tests include a finger to nose test, a walk and turn test, a modified Romberg balance test, and a one leg stand test on the suspect;
- reading the output data in a microcontroller;
- formatting a record of the output data;
- storing the formatted record in a memory;
- formatting a record of the output data for Bluetooth transmission;
- sending the formatted record to a computing device; and
- computing whether the suspect is *cannabis* impaired based upon the data record of the suspect's movement during the psychophysical tests as sensed by the triaxial gyroscope assembly, wherein the output data record is generated by use of root sum squared (RSS) equation on the data indicative of the angular rate of the suspect's movement versus time and quantifies the suspect's number of failures on each test used as demonstrated by abnormal and excessive suspect movement test data obtained during performance of the tests that indicate *cannabis* impairment rather than THC content of the suspect.

10. The method of claim 9, wherein the suspect's movement is associated with sway as defined in the one leg stand test as an indicator of the *cannabis* impairment.

11. The method of claim 9, wherein the suspect's movement is associated with gait as defined in the walk and turn test as an indicator of the *cannabis* impairment.

12. The method of claim 9, wherein the suspect's movement is associated with sway and balance as defined in the modified Romberg balance test as an indicator of the *cannabis* impairment.

13. The method of claim 9, wherein the suspect's movement is associated with hand movement as defined in the finger to nose test as an indicator of the *cannabis* impairment.

14. The method of claim 9, wherein the step of computing the suspect's movement is executed in the triaxial gyroscope assembly.

15. The method of claim 9, wherein the step of computing signals indicative of the suspect's movement is executed in the computing device.

16. The method of claim 9, further comprising computing the Root Sum Squared (RSS) equation of the Bluetooth record in a computing device.

* * * * *